United States Patent
Scheele et al.

(10) Patent No.: US 9,907,494 B2
(45) Date of Patent: Mar. 6, 2018

(54) NIRS DEVICE WITH OPTICAL WAVELENGTH AND PATH LENGTH CORRECTION

(75) Inventors: Bryan J. Scheele, Hutchinson, MN (US); Nicholas H. Finstrom, Hopkins, MN (US); Roger W. Schmitz, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 1400 days.

(21) Appl. No.: 13/449,889

(22) Filed: Apr. 18, 2012

(65) Prior Publication Data

US 2013/0281803 A1    Oct. 24, 2013

(51) Int. Cl.
*A61B 5/1455*    (2006.01)

(52) U.S. Cl.
CPC ........ *A61B 5/14552* (2013.01); *A61B 5/1455* (2013.01); *A61B 5/14551* (2013.01)

(58) Field of Classification Search
CPC .............. A61B 5/1455; A61B 5/14551; A61B 5/14552; A61B 5/0059; A61B 5/72
USPC ....... 600/310, 316, 322, 323, 326, 328, 338, 600/340, 344, 473, 476; 356/41
See application file for complete search history.

(56) References Cited

U.S. PATENT DOCUMENTS

| | | |
|---|---|---|
| 3,972,329 A | 8/1976 | Kaufman |
| 4,223,680 A | 9/1980 | Jobsis |
| 4,537,197 A | 8/1985 | Hulka |
| 4,570,638 A | 2/1986 | Stoddart et al. |
| 4,653,498 A | 3/1987 | New, Jr. et al. |
| 4,768,516 A | 9/1988 | Stoddart et al. |
| 4,817,623 A | 4/1989 | Stoddart et al. |
| 4,825,879 A | 5/1989 | Tan et al. |
| 4,830,014 A | 5/1989 | Goodman et al. |
| 4,865,038 A | 9/1989 | Rich et al. |
| 4,932,684 A | 6/1990 | Vermeulen |

(Continued)

FOREIGN PATENT DOCUMENTS

| | | |
|---|---|---|
| EP | 0127947 B1 | 8/1990 |
| EP | 0587009 A1 | 3/1994 |

(Continued)

OTHER PUBLICATIONS

Hiraoka, et al. "A Monte Carlo investigation of optical pathlength in inhomogeneous tissue and its application to near-infrared spectroscopy", Phys. Med. Biol. 38 (1993) 1859-1876.*

(Continued)

*Primary Examiner* — Eric Winakur
*Assistant Examiner* — Chu Chuan (JJ) Liu
(74) *Attorney, Agent, or Firm* — Nixon Peabody LLP

(57) ABSTRACT

A near infrared spectrometer and method for wavelength and path length correction are disclosed. The spectrometer includes a number of photodiodes that transmit broadband near infrared measurement light into the tissue and at least one broadband detector which measures the light signal transmitted through the tissue. A processor estimates chromophore concentrations through a comparison of measured light attenuation and modeled light attenuation. The light attenuation model utilizes a light path length distribution derived from a Monte Carlo model and accounts for the spectral shape of the light source as a function of temperature.

8 Claims, 10 Drawing Sheets

(56) References Cited

U.S. PATENT DOCUMENTS

| | | | |
|---|---|---|---|
| 4,964,408 A | 10/1990 | Hink et al. | |
| 5,094,240 A | 3/1992 | Muz | |
| 5,111,817 A | 5/1992 | Clark et al. | |
| 5,139,025 A | 8/1992 | Lewis et al. | |
| 5,222,495 A | 6/1993 | Clarke et al. | |
| 5,224,478 A | 7/1993 | Sakai et al. | |
| 5,237,994 A | 8/1993 | Goldberger | |
| 5,267,563 A | 12/1993 | Swedlow et al. | |
| 5,348,003 A * | 9/1994 | Caro | 600/310 |
| 5,349,961 A | 9/1994 | Stoddart et al. | |
| 5,392,783 A | 2/1995 | Fogarty et al. | |
| 5,402,777 A | 4/1995 | Warring et al. | |
| 5,411,023 A | 5/1995 | Morris, Sr. et al. | |
| 5,477,853 A | 12/1995 | Farkas et al. | |
| 5,482,034 A | 1/1996 | Lewis et al. | |
| 5,529,065 A * | 6/1996 | Tsuchiya | 600/310 |
| 5,584,296 A | 12/1996 | Cui et al. | |
| 5,642,733 A | 7/1997 | Archibald et al. | |
| 5,680,857 A | 10/1997 | Pelikan et al. | |
| 5,842,982 A | 12/1998 | Mannheimer | |
| 5,851,178 A * | 12/1998 | Aronow | 600/323 |
| 5,879,294 A * | 3/1999 | Anderson et al. | 600/310 |
| 5,879,373 A | 3/1999 | Roper et al. | |
| 5,902,235 A | 5/1999 | Lewis et al. | |
| 5,931,779 A | 8/1999 | Arakaki et al. | |
| 6,006,119 A | 12/1999 | Soller et al. | |
| 6,061,584 A | 5/2000 | Lovejoy et al. | |
| 6,091,975 A | 7/2000 | Daddona et al. | |
| 6,095,974 A | 8/2000 | Shemwell et al. | |
| 6,101,405 A | 8/2000 | Yasuda et al. | |
| 6,304,767 B1 | 10/2001 | Soller et al. | |
| 6,377,829 B1 | 4/2002 | Al Ali | |
| 6,377,840 B1 | 4/2002 | Gritsenko et al. | |
| 6,381,489 B1 | 4/2002 | Ashibe | |
| 6,415,167 B1 | 7/2002 | Blank et al. | |
| 6,428,515 B1 | 8/2002 | Bierman et al. | |
| 6,456,862 B2 | 9/2002 | Benni | |
| 6,473,632 B1 | 10/2002 | Myers | |
| 6,487,343 B1 | 11/2002 | Lewandowski et al. | |
| 6,527,711 B1 | 3/2003 | Stivoric | |
| 6,556,851 B1 | 4/2003 | Ott et al. | |
| 6,564,088 B1 | 5/2003 | Soller et al. | |
| 6,615,065 B1 | 9/2003 | Barrett et al. | |
| 6,671,532 B1 | 12/2003 | Fudge et al. | |
| 6,725,075 B2 | 4/2004 | Al Ali | |
| 6,766,188 B2 | 7/2004 | Soller | |
| 6,807,202 B1 | 10/2004 | Plamper et al. | |
| 6,839,579 B1 | 1/2005 | Chin | |
| 6,839,583 B1 | 1/2005 | Lewandowski et al. | |
| 6,892,006 B2 | 5/2005 | Lewandowski et al. | |
| 7,047,054 B2 | 5/2006 | Benni | |
| 7,072,701 B2 | 7/2006 | Chen et al. | |
| 7,239,385 B2 | 7/2007 | Schmitz et al. | |
| 7,239,901 B2 | 7/2007 | Gritsenko | |
| 7,313,427 B2 | 12/2007 | Benni | |
| 7,460,897 B1 | 12/2008 | Flessland et al. | |
| 7,532,919 B2 | 5/2009 | Soyemi et al. | |
| 7,613,489 B2 | 11/2009 | Myers | |
| 7,616,303 B2 | 11/2009 | Yang et al. | |
| 7,668,587 B2 | 2/2010 | Benaron et al. | |
| 7,705,608 B2 | 4/2010 | Mueller | |
| 7,881,892 B2 | 2/2011 | Soyemi et al. | |
| 8,000,775 B2 | 8/2011 | Pogue et al. | |
| 2002/0038080 A1 | 3/2002 | Makarewicz et al. | |
| 2002/0165440 A1 | 11/2002 | Mason et al. | |
| 2003/0069484 A1 | 4/2003 | Blank et al. | |
| 2003/0166998 A1 | 9/2003 | Lowery et al. | |
| 2003/0181799 A1 | 9/2003 | Lindekugel et al. | |
| 2004/0147822 A1 | 7/2004 | Al Ali et al. | |
| 2004/0167382 A1 | 8/2004 | Gardner et al. | |
| 2005/0054908 A1 | 3/2005 | Blank et al. | |
| 2006/0111622 A1 | 5/2006 | Merritt et al. | |
| 2006/0217608 A1 * | 9/2006 | Fein et al. | 600/323 |
| 2007/0105212 A1 | 5/2007 | Oldham et al. | |
| 2008/0242958 A1 | 10/2008 | Al-Ali et al. | |
| 2009/0281403 A1 | 11/2009 | Benni | |
| 2011/0102791 A1 | 5/2011 | Johnson et al. | |

FOREIGN PATENT DOCUMENTS

| | | |
|---|---|---|
| EP | 0568380 B1 | 9/1997 |
| EP | 0816829 A2 | 1/1998 |
| EP | 0816829 B1 | 8/2003 |
| JP | 2004351107 A | 4/2012 |
| WO | WO1997001985 A1 | 1/1997 |
| WO | WO2001078587 A2 | 10/2001 |
| WO | WO2002028274 A1 | 4/2002 |
| WO | WO2003024303 A2 | 3/2003 |
| WO | WO2005027720 A2 | 3/2005 |
| WO | WO2011070357 A1 | 6/2011 |

OTHER PUBLICATIONS

Bartels, Sebastiaan A. et al., "Multi-site and multi-depth near-infrared spectroscopy in a model of simulated (central) hypovolemia: lower body negative pressure", Intensive Care Med (2011) 37:671-677.

Beekley, Alec C. et al., "Continuous Noninvasive Tissue Oximetry in the Early Evaluation of the Combat Casualty: A Prospective Study", The Journal of Trauma Injury, Infection, and Critical Care, vol. 69, No. 1, July Supplement 2010, S14-S25.

Bezemer, Rick et al., "Simultaneous multi-depth assessment of tissue oxygen saturation in thenar and forearm using near-infrared spectroscopy during a simple cardiovascular challenge", Critical Care 2009, 13(Supp 5), pp. 1-5.

Bruce A. Crookes, et al., "Can Near-Infrared Spectroscopy Identify the Severity of Shock in Trauma Patients?", The Journal of Trauma Injury, Infection, and Critical Care, vol. 58, No. 4, Apr. 2005, pp. 806-816, XP009073413.

Bruce A. McKinley, et al., "Tissue Hemoglobin 02 Saturation during Resuscitation of Traumatic Shock Monitored Using Near Infrared Spectrometry", The Journal of Trauma Injury, Infection, and Critical Care, vol. 48, No. 4, Apr. 2000, pp. 637-642, XP009073412.

Cohen, Stephen M. et al., "Tissue Oxygen Saturation predicts the Development of Organ Dysfunction During Traumatic Shock Resuscitation", The Journal of Trauma Injury, Infection and Critical Care, Jan. 2007, vol. 62, No. 1, pp. 44-55.

Davis, Roger et al., "Broadband Integrated Transmittances" Army Research Laboratory, Feb. 1995, 141 pages.

Doerschug, Kevin C. et al., "Impairments in microvascular reactivity are related to organ failure in human sepsis", Am J Physiol Heart Circ Physiol 293: H1065-H1071, 2007.

Elwell, Clare et al., "Near Infrared Spectroscopy", biomedical Optics Research Laboratory, downloaded from http://www.ucl.ac.uk/medphys/research/borl/intro/nirs on Mar. 13, 2012, 8 pages.

Extended European Search Report issued in EP 10010019, completed Nov. 12, 2010, 9 pages.

Graaf, R. et al., "Condensed Monte Carlo simulations for the description of light transport", Applied Optics, vol. 32, No. 4, Feb. 1, 1993, 9 pages.

Hernandez, Sergio et al., "Diffuse reflectance spectroscopy characterization of hemoglobin and intralipid solutions: in vitro measurements with continuous variation of absorption and scattering", Journal of Biomedical Optics, vol. 14, No. 3, May-Jun. 2009, 6 pages.

International Search Report and Written Opinion issued in PCT/US2013/036186, dated Jul. 19, 2013, 13 pages.

Liu, Hongyuan et al., "Design of a tissue oxygenation monitor and verification on human skin", Clinical and biomedical Spectroscopy and Imaging II, Proc of SPIE vol. 8087, copyright 2011.

Matcher, S. J. et al., "Absolute Quantification of Deoxyhaemoglobin Concentration in Tissue Near infrared Spectroscopy", Phys. Med. Biol. 39 (1994) 1295-1312.

Matcher, S. J. et al. "Performance Comparison of Several Published Tissue Near-Infrared Spectroscopy Algorithms", Analytical Biochemistry 227, 54-68 (1995).

(56) References Cited

OTHER PUBLICATIONS

Moore, Frederick A. et al., "Massive Transfusion in Trauma Patients: tissue Hemoglobin Oxygen Saturation Predicts Poor Outcome", The Journal of Trauma Injury, Infection and Critical Care, Apr. 2008, vol. 64, No. 4, pp. 1010-1023.
Myers, Dean E. et al. "Noninvasive method for measuring local hemoglobin oxygen saturation in tissue using wide gap second derivative near-infrared spectroscopy", Journal of Biomedical Optics, vol. 10, No. 3, Jun. 7, 2005, 18 pages.
Partial European Search Report issued in EP 10010021, completed Nov. 9, 2010, 3 pages.
Pifferi, Antonia et al., "Real-time method for fitting time-resolved reflectance and transmittance measurements with a Monte Carlo model", Applied Optics, vol. 38, No. 13 May 1, 1998, 7 pages.
Poeze, M. "Tissue-oxygenation assessment using near-infrared spectroscopy during severe sepsis: confounding effects of tissue edema on St02 values", Intensive Care Med (2006) 32:788-789.
Prahl, Scott, "Optical Absorption of Hemoglobin", downloaded from http://omlc.ogi.edu/spectra/hemoglobin/ on Mar. 13, 2012, 3 pages.
Sagraves, Scott G. et al., "Tissue Oxygenation Monitoring in the Field: A New EMS Vital Sign", The Journal of Trauma Injury, Infection and Critical Care, vol. 67, No. 3, Sep. 2009, pp. 441-444.
Sassaroli, Angelo et al., "Comment on the modified Beer-Lambert law for scattering media", Phys. Med. Bio. 49 (2004) N255-N257.
Skarda, David E., "Dynamic near-infrared Spectroscopy Measurements in Patients with Severe Sepsis", Shock, 2007, vol. 27, No. 4, pp. 348-357.
Tsuchiya, Yataka, "Photon path distribution and optical responses of turbid media: theoretical analysis based on the microscopic Beer-Lambert law", Phys. Med. Biol. 46(2001)2067-2084.
Wang, Lihong et al., MCML—Monte Carlo modeling of light transport in multi-layered tissues, Computer Methods and Programs in biomedicine 47 (1995) 131-146.

\* cited by examiner

NIRS DEVICE WITH OPTICAL WAVELENGTH AND PATH LENGTH CORRECTION

TECHNICAL FIELD

The present disclosure relates generally to devices, systems, and methods for measuring tissue oxygenation in body tissue. More specifically, the present disclosure pertains to a near infrared spectrometer and method for optical wavelength and path length correction.

BACKGROUND

Tissue oxygenation is often used as an indicator of perfusion status in patients experiencing undifferentiated shock. High risk patients who receive continuous monitoring of tissue oxygenation from the trauma bay through X-ray and CT imaging as well as other procedures have been shown to receive effective interventions sooner, resulting in significant reductions in ICU admission, length of stay, morbidity, and mortality.

Near Infrared Spectroscopy (NIRS) is one technique used for non-invasively measuring tissue oxygenation. To measure tissue oxygenation, NIRS systems use complex mathematical algorithms that relate light attenuation, measured at multiple wavelengths, to the concentration of different hemoglobin forms, such as oxyhemoglobin ($HbO_2$) and deoxyhemoglobin (HHb). The concentration of these hemoglobin forms or their calculated oxygen saturation ratio ($[HbO_2]/[HbO_2+HHb]$), defined as saturated oxygen level or "$StO_2$," provides an indication of how much oxygen is available to the tissue. A clinician may use these tissue oxygen measurements to evaluate a patient's health status and make treatment decisions.

NIRS devices employ a light source that illuminates tissue at specific wavelengths of light, typically between 650 nm to 1000 nm, and at least one photodetector that measures the amount of light exiting the tissue within a given area. An example of a NIRS spectrometer is described, for example, in U.S. Pat. No. 7,239,901, the contents of which are incorporated herein by reference in their entirety for all purposes.

During operation, the amount of light exiting the tissue is compared to the amount of light emitted into the tissue in order to measure the amount of light lost in the tissue, which is defined as light attenuation. In tissue, light attenuation occurs from absorption and scattering events. Light absorbing molecules, called chromophores, convert light to heat energy thus reducing the amount of detected light. Light scattering molecules, such as tissue cells and organelles, refract light thereby changing the direction and hence path length that the light travels. Although some scattering is required to direct light to the detector in a reflectance probe configuration, the scattering effect on the light path limits and reduces the amount of light that eventually exits the tissue where the photodetector is placed. A reduction in detected light, either from absorption or scattering events, therefore increases the amount of light attenuation measured with a NIRS spectrometer.

SUMMARY

The present disclosure pertains to a NIRS spectrometer and method for wavelength and path length correction. A near infrared spectrometer for sensing tissue oxygen measurements in body tissue in accordance with an exemplary embodiment comprises a plurality of light sources configured to emit broadband, near-infrared measurement light into body tissue; at least one broadband photodetector configured for sensing at least a portion of the measurement light reflected back from the body tissue; a means for modeling light attenuations within the body tissue; and a means for estimating at least one tissue chromophore concentration within the body tissue by comparing attenuations of the sensed measurement light reflected back from the body tissue to the modeled light attenuations.

A NIRS spectrometer for sensing tissue oxygen measurements in body tissue in accordance with another exemplary embodiment comprises a plurality of light sources configured to emit broadband, near-infrared measurement light into body tissue; at least one broadband photodetector configured for sensing at least a portion of the measurement light reflected back from the body tissue; a temperature sensor configured for sensing a temperature of each light source; a light attenuation model configured for modeling light attenuations within the body tissue based at least in part on the temperature sensed by the temperature sensor; a processor configured for estimating at least one tissue chromophore concentration within the body tissue by comparing attenuations of the sensed measurement light reflected back from the body tissue to modeled light attenuations from the light attenuation model. In some embodiments, the processor is configured to sum the attenuations of the modeled measurement light at a plurality of wavelength increments, the wavelength increments being smaller than a spectral width of each light source and a responsivity of the at least one broadband photodetector.

A method for determining one or more tissue oxygen measurements in body tissue in accordance with an exemplary embodiment comprises coupling a spectrometer to a tissue of interest, the spectrometer including a plurality of light sources configured to emit broadband, near-infrared measurement light into the body tissue and at least one broadband photodetector configured for sensing at least a portion of the measurement light reflected back from the body tissue; measuring the attenuation of the measurement light reflected back from the body tissue; predicting light attenuation within the body tissue using a light attenuation model; and estimating at least one tissue chromophore concentration within the body tissue by comparing the attenuation of the measurement light reflected back from the body tissue to the predicted light attenuation. In some embodiments, the light attenuation model is configured to sum the attenuations of the modeled light at a plurality of wavelength increments that are smaller than a spectral width of each light source and a responsivity of the at least one broadband photodetector While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
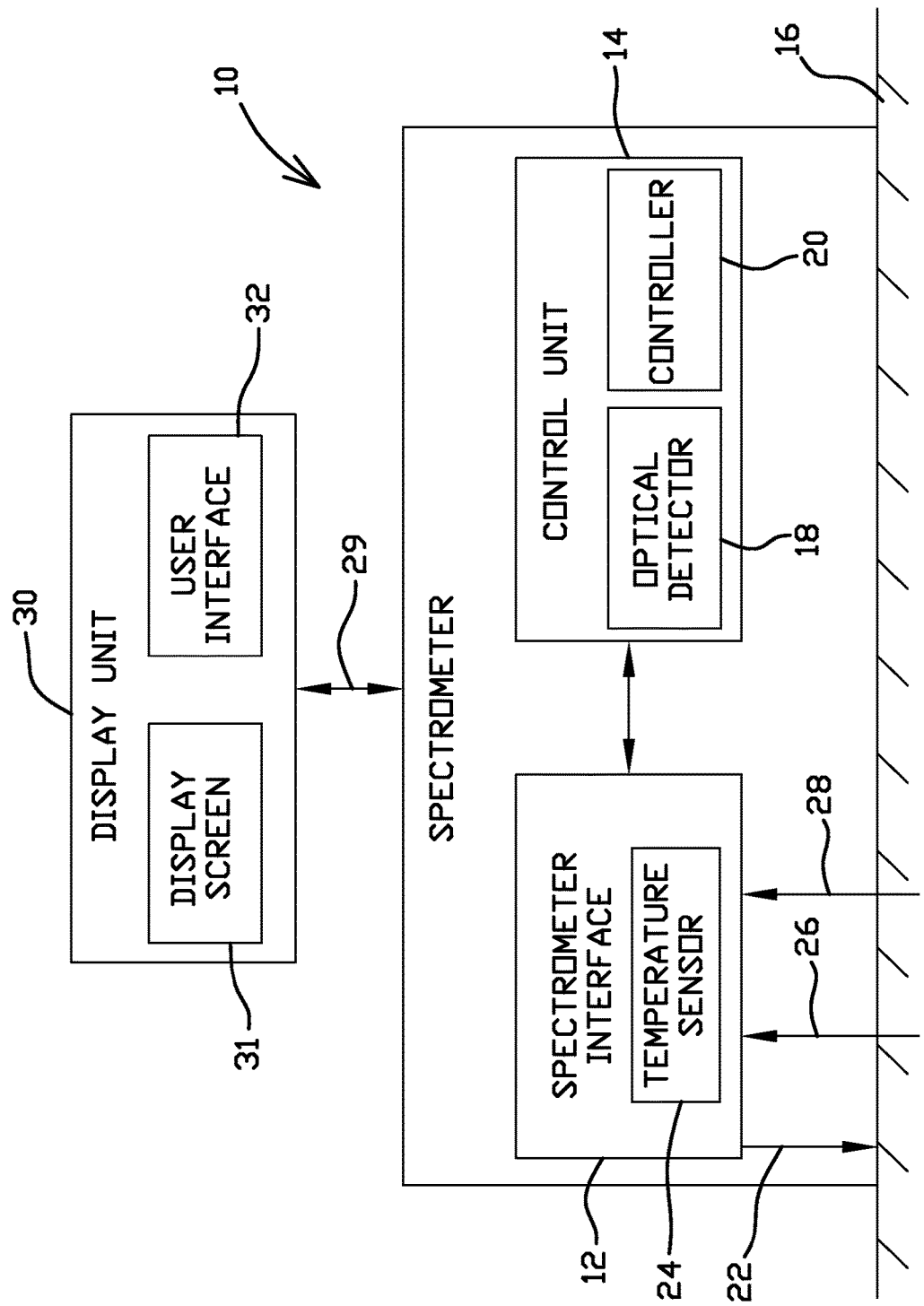
FIG. 1 is a block diagram of a near infrared spectrometer in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a block diagram of a spectrometer 10 in accordance with an illustrative embodiment. As shown in FIG. 1, the spectrometer 10 includes a spectrometer interface 12 and a control unit 14. The spectrometer interface 12 includes a number of light sources and/or light pathways for directing light into the tissue 16 under study, and for subsequently collecting measurement light returned back from the tissue 16. In some embodiments, the spectrometer interface 12, control unit 14, and/or other spectrometer components are integrated into a single, hand-held device, which eliminates the need for separate fiber-optic cables for transmitting light back and forth between the spectrometer interface 12 and the control unit 14. In one embodiment, the circuitry for the spectrometer interface 12 is located on the same board as the circuitry for the control unit 14, and the spectrometer 10 is configured to couple directly to the patient's tissue 16 without requiring the attachment of a separate optical probe. In other embodiments, the light sources are located in the spectrometer interface 12, and light pathways are carried in a fiber-optic cable for delivering and receiving light back and forth between the spectrometer interface 12 and a separate optical probe that connects to the patient's tissue 16.

In the embodiment of FIG. 1, the control unit 14 includes an optical detector 18 and a controller 20. Light 22 generated by the controller 20 is delivered into the patient's tissue 16 via the spectrometer interface 12. In some embodiments, a temperature sensor 24 located at or near the light sources is used to measure the temperature of the light sources, as discussed further herein. Measurement light signals 26 collected by the optical detector 18 as well as a reference light signal 28 obtained from the tissue, in turn, are transmitted via the spectrometer interface 12 to the optical detector 18. Based on these signals 26, 28, the optical detector 18 produces electrical signals representative of the light signals at each wavelength of interest. The controller 20 then processes these signals along with the signal from the temperature sensor 24 to generate data representative of the measured tissue parameter(s), including the saturated oxygen level ($StO_2$) within the tissue. An example method for determining tissue parameter data such as $StO_2$ is described further herein with respect to FIG. 4. Other techniques can also be used for processing the signals and generating data representative of tissue oxygenation.

An electrical connector 29 connects the spectrometer 10 to a display unit 30, which can be used to display the tissue measurement data in various user-defined formats. In some embodiments, the display unit 30 includes an LCD display screen 31 and a user-interface 32. The display unit 30 can also include other functionality for operating the spectrometer 10, including a power source for supplying power to the spectrometer 10 and/or a computer interface port for connecting the spectrometer 10 to another device for further analysis and/or storage of the tissue oxygenation data.

Figure 2:
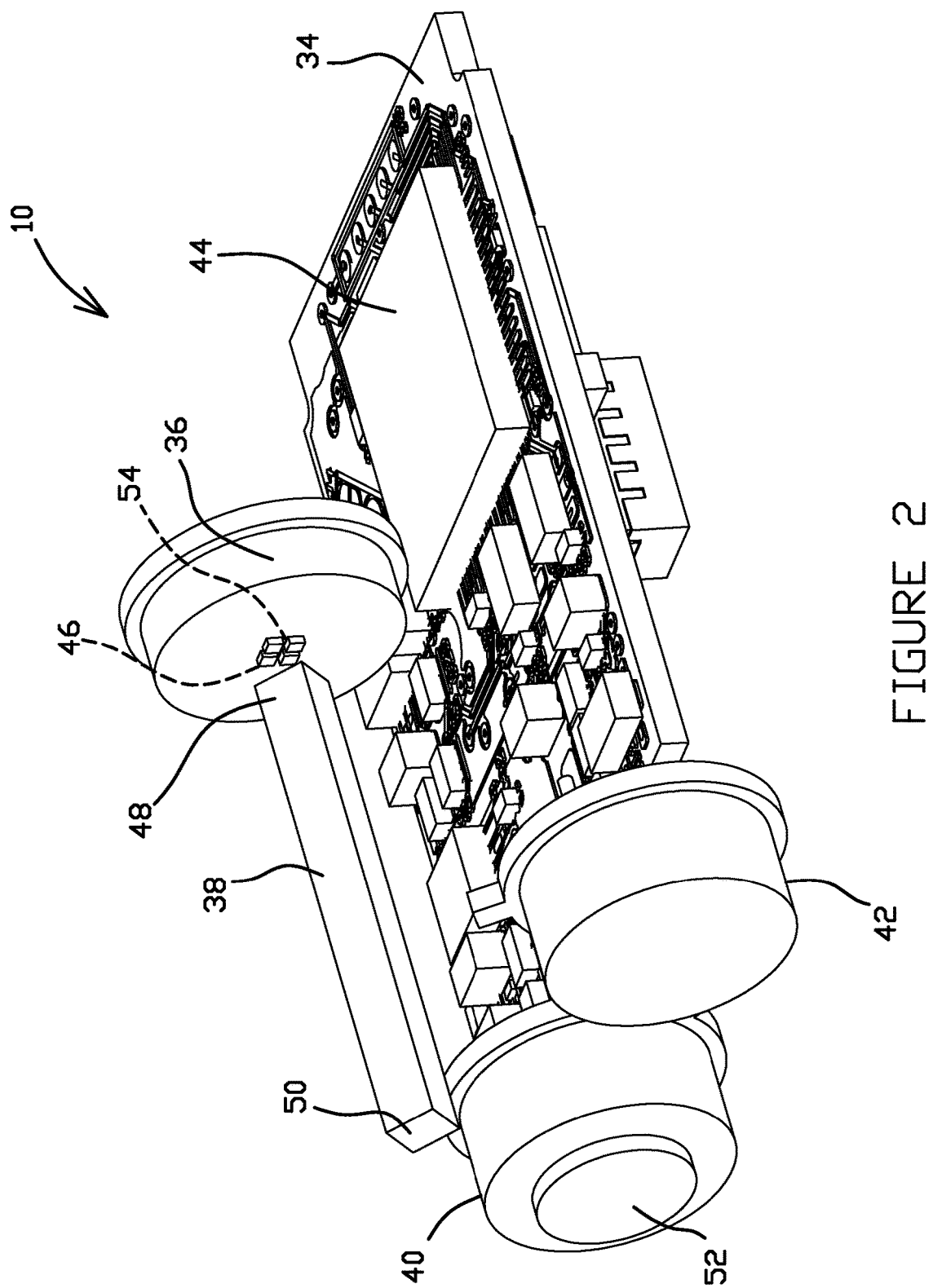
FIG. 2 is a perspective view showing several illustrative components of the spectrometer of FIG. 1.

FIG. 2 is a perspective view showing several illustrative components of the spectrometer 10 of FIG. 1. FIG. 2 may represent, for example, several illustrative components of the spectrometer interface 12 and control unit 14 of FIG. 1. As shown in FIG. 2, and in some embodiments, the spectrometer 10 includes a spectrometer board 34, a light source board 36, a mixer 38, a first photodetector 40, and a second photodetector 42.

The spectrometer board 34 includes circuitry for operating the light source board 36 and photodetectors 40, 42, and for converting analog signals from the photodetectors 40, 42 into corresponding digital signals. In some embodiments, the spectrometer board 34 includes programmable firmware used to convert these digital signals into attenuation signals, which as discussed further herein, can be used to determine an estimated value of saturated tissue oxygenation ($StO_2$), oxyhemoglobin ($HbO_2$) and deoxyhemoglobin (HHb), as well as other desired tissue oxygen parameters. A processor 44 is configured to process the measurement and reference light signals sensed by the photodetectors and determine one or more associated tissue oxygen parameters.

The light source board 36 includes a number of photodiodes 46 (e.g., light-emitting diodes (LEDs)) that emit near-infrared broadband measurement radiation that is generally centered at wavelengths of 680 nm, 720 nm, 760 nm, and 800 nm. The LEDs 46 are each optically coupled to the input end 48 of the mixer 38, and are configured to emit radiation directly into mixer 38 in lieu of first passing the radiation through light source conditioning optics prior to entry into the mixer 38, as is done by some NIRS spectrometer devices. For example, the LEDs 46 are coupled to the input end 48 of the mixer 38 without the use of interference filters, focusing lenses, and/or fiber-optic bundles sometimes used to collimate, filter, and direct the emitted radiation from each LED source into the mixer 38. The output end 50 of the mixer 38, in turn, is optically coupled directly to the tissue to be analyzed without being passed through a fiber optic cable, as is also done by some NIRS spectrometer devices. In some embodiments, film couplers may be used to prevent instabilities in optical transmission that may be caused by interference effects at the input and output ends 48, 50 of the mixer 38. Several example film couplers that are suitable for this purpose are described further in U.S. Patent Publication No. 2011/0102791, the contents of which are incorporated herein by reference in their entirety for all purposes.

From the perspective of spectrometer size, the light source conditioning optics used in some NIRS spectrometer devices consume a large portion of the total spectrometer size, and increase the overall complexity of the device. The elimination of the light source conditioning optics in the spectrometer 10 of FIGS. 1-2 reduces the cost and complexity of the spectrometer 10, and allows the LEDs 46 to be positioned in close proximity together on the light source board 36. For example, the collimating lenses, interference filters, and focusing lenses used to collimate, filter, and focus the light in some NIRS devices typically require precision optical mounts to precisely position these components relative to each other, increasing the cost and complexity of the device. Moreover, the elimination of fiber optics on the output end 50 of the mixer 38 allows the spectrometer 10 to be directly coupled to the tissue, eliminating the need for a separate optical probe.

The mixer 38 is made from a suitable glass, and is sized and shaped to equally distribute the intensity of the measurement radiation output, thereby creating a spatially uniform illumination at the output 50 from a highly, non-spatially uniform source at the input 48. An example of a suitable glass is Schott SF11® glass, which does not degrade in medical x-ray environments and which provides desirable optical (e.g., transmittance, refractive index, dispersion), mechanical, and thermal properties over the range of wavelengths used by the LEDs 46. In the embodiment shown, the mixer 38 has an essentially constant, rectangular cross-section along its length. Other polygonal cross-sectional shapes such as, for example, hexagonal and/or octagonal, may also be used. The cross-sectional shape of the mixer 38 may also vary between the input and output ends 48, 50.

In some embodiments, the first photodetector 40 is coupled to the spectrometer board 34, and is configured to convert the output light signal received from the tissue into an analog electrical signal for processing via the processor 44. An ambient light filter 52 is configured to filter out any light signal that is not within the spectral range of interest. In some embodiments, for example, the filter 52 is configured as a passband filter to filter wavelengths shorter than approximately 670 nm and larger than approximately 810 nm. The ambient light filter 52 may filter out light at different optical passbands, however, depending on the specific wavelength range of the light transmitted by the LEDs 46.

In some embodiments, the second photodetector 42 is similarly coupled to the spectrometer board 34, and is configured to receive a portion of the light taken through a shorter path of the tissue than the measurement light detected by the first photodetector 40. In certain embodiments, and as shown in FIG. 2, the first and second photodetectors 40, 42 are each arranged side-by-side and are positioned at a known, fixed distance apart from each other.

In use, the coupling of the first and second photodetectors 40, 42 directly to the tissue eliminates the need for fiber-optic connections between the photodetectors 40, 42 and the tissue. The direct coupling of the second photodetector 42 to the tissue also eliminates the need for a feedback attenuator, which is used by some NIRS spectrometer devices to reduce the magnitude of the feedback signal to be compatible with the dynamic range of a feedback photodetector. The need for such attenuation typically arises as a result of coupling the output end of the mixer through a feedback fiber optic to the feedback photodetector in lieu of obtaining the feedback light from the tissue itself, as is done with the spectrometer 10 of FIG. 2.

To compensate for the elimination of the light source condition optics, including the presence of interference filters sometimes used in NIRS spectrometer devices for controlling the spectral properties of the emitted light, a temperature sensor 54 on the light source board 36 can be used to monitor the temperature of the LEDs 46 during operation. In some embodiments, the temperature sensor 54 comprises a thermistor or thermocouple that outputs a temperature signal indicative of the operating temperature of the LEDs 46. Multiple temperature sensors 54 can also be used to sense the operating temperature of the LEDs 46. Using the temperature signals, and as discussed further herein, the processor 44 can be configured to determine the temperature dependent spectral shape of the LEDs 46 and predict the amount of light attenuation in the tissue.

When a chromophore exists in a non-scattering medium, the Beer-Lambert Law in equation (1) below defines the absorption of light at one wavelength ($A_\lambda$) in terms of the measured light intensity entering and exiting the medium ($I_{in,\lambda}$ and $I_{out,\lambda}$):

$$A_\lambda = \ln\left(\frac{I_{in,\lambda}}{I_{out,\lambda}}\right) = \varepsilon_\lambda C L \quad (1)$$

where:

$\epsilon_\lambda$ is the absorption coefficient at a specific wavelength, defining the attenuation magnitude per unit path length per unit concentration for a specific chromophore;

C is the concentration of the chromophore; and

L is the optical path length representing the linear distance that the light traveled within the non-scattering medium.

In a scattering medium such as body tissue, however, optical scattering produces many different optical path lengths for the light that travels through tissue and reaches the photodetectors 40, 42. These scattered path lengths are characterized as being longer than the path lengths that would otherwise exist if scattering did not occur. Additionally, in tissue, the intensity weighted path length distributions begin to vary with wavelength since absorption magnitude, which is wavelength dependent via the absorption coefficient ($\epsilon_\lambda$), increases the probability that the longer optical path lengths within the distribution of all path lengths are more attenuated before reaching the photodetectors 40, 42.

Figure 3:
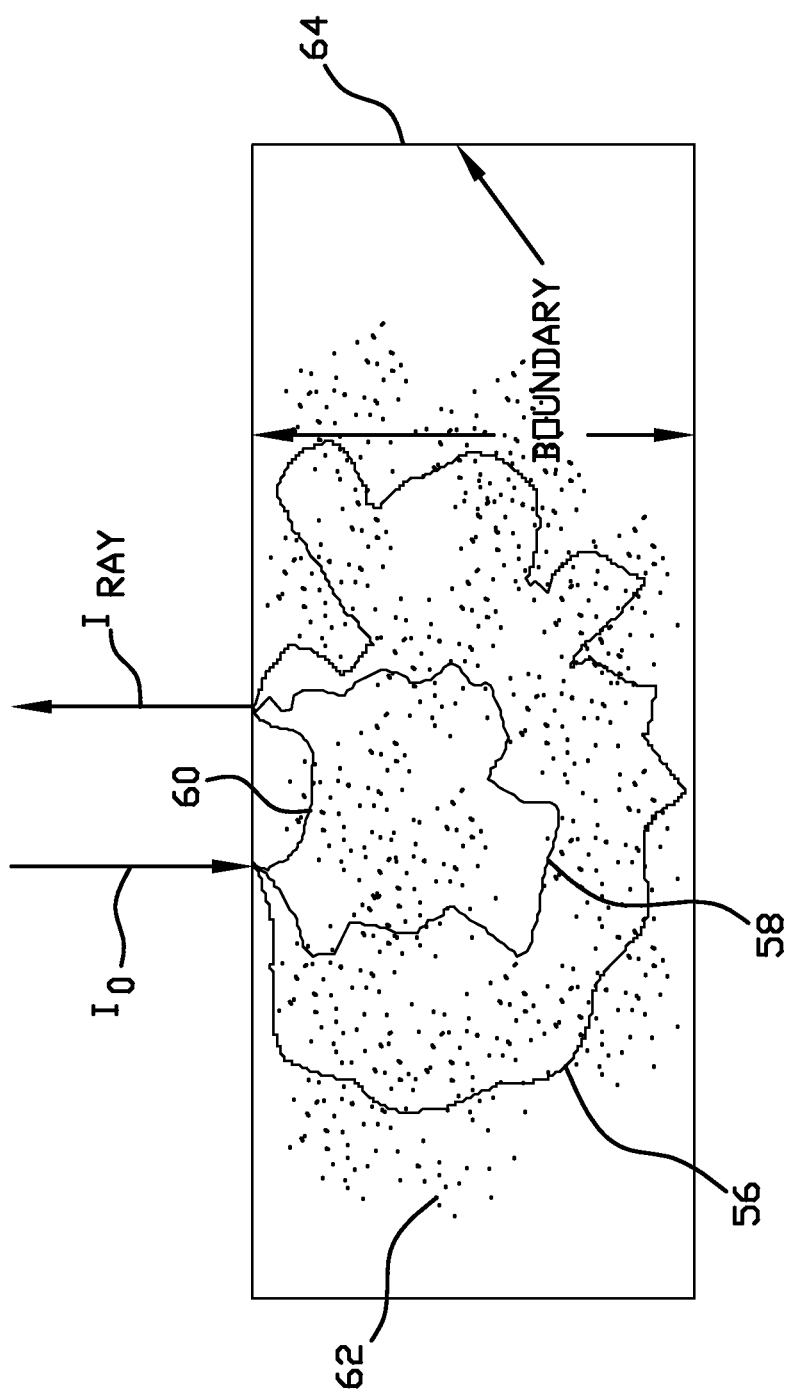
FIG. 3 is a schematic view depicting a simulation of light rays or photons propagating through a scattering medium such as tissue.

An example of this phenomenon in a scattering medium can be seen in FIG. 3, which depicts a Monte Carlo (MC) light simulation of three light rays or photons entering into a non-linear scattering medium such as body tissue. As can be seen in FIG. 3, three example light rays 56, 58, 60 are transmitted into tissue 62 having a boundary volume defined by boundary layer 64. The emitted light ($I_0$) emitted by the light source and the received light ($I_{RAY}$) sensed by the photodetector are at a fixed distance apart from each other to permit reflectance mode measurements to be taken within the tissue 62.

When the light rays 56, 58, 60 enter into the tissue 62, the scattering characteristics of the tissue 62 cause each ray 56, 58, 60 to traverse a different optical path within the tissue 62, as shown. The variance in path lengths of the rays 56, 58, 60 in a scattering medium are the result of a number of different factors, including the scattering properties, geometry, and the boundary optical properties of the medium.

An effective optical path length $L_{\mathit{eff},\lambda}$ can be defined generally as an equivalent uniform path length in a non-scattering medium that would yield the same attenuation as the varying path length distribution in the scattering medium. As set forth in equation (2) below, $L_{\mathit{eff},\lambda}$ can be determined by the product of a wavelength dependent differential path length factor ($\alpha_\lambda$) and the optical path length for zero scattering (L):

$$L_{\mathit{eff},\lambda} = \alpha_\lambda(L) \qquad (2)$$

For tissue spectrometers where the light source and photodetector are located on the same tissue surface (i.e., reflectance mode positioning), the optical path length for zero scattering (L) in equation (2) represents the separation distance between the light source and photodetector. Thus as separation distance between the light source and photodetector increases, the optical path length also increases. If a chromophore or combination of chromophores strongly absorbs a particular wavelength of light, then that wavelength of light will have a shorter effective optical path length ($L_{\mathit{eff},\lambda}$).

In addition to the optical path length being different in a scattering tissue medium, scattering attenuation ($A_{\mathit{scat},\lambda}$) also contributes to total light attenuation. Scattering attenuation is wavelength dependent because in a scattering tissue medium the shorter wavelengths of light are more effectively scattered than longer wavelengths of light, which decreases the probability that the light reaches the photodetector. Thus in body tissue, a modified version of the Beer-Lambert Law is applicable, as expressed in equation (3) below:

$$A_\lambda = \ln\left(\frac{I_{\mathit{in},\lambda}}{I_{\mathit{out},\lambda}}\right) = \varepsilon_\lambda(C) L_{\mathit{eff},\lambda} + A_{\mathit{scat},\lambda} \qquad (3)$$

For a measurement of tissue oxygenation, the detected wavelengths used in equation (3) above can be selected such that the attenuation measurements are sensitive and specific to oxyhemoglobin and deoxyhemoglobin and less sensitive and specific to background absorbers that could confound measurement accuracy, such as fat, water, and melanin. In some cases, these background absorbers may also not require measurement since their concentration levels may have limited or no clinical utility.

In the NIRS wavelength region, both hemoglobin and other background absorbers have broad overlapping absorption spectra. A more accurate tissue attenuation model can include concentration and absorptivity coefficient terms for all chromophores that significantly contribute to the total light attenuation at the measured light wavelengths. Also, since fat and melanin are generally located above muscle tissue, the effective light path length for these chromophores can be different than that for the muscle tissue chromophores; specifically, oxyhemoglobin ($HbO_2$), deoxyhemoglobin (HHb), oxymyoglobin ($MyO_2$), deoxymyoglobin (My) and water ($H_2O$). To account for multiple absorbers and different effective light path lengths associated with layered or non-homogenous tissue such as muscle, fat, and skin, the following solution for the modified Beer-Lambert Law is applicable:

$$A_\lambda = (\varepsilon_{HbO2\lambda} C_{HbO2} + \varepsilon_{Hb\lambda} C_{Hb} + \varepsilon_{MyO2\lambda} C_{MyO2} + \varepsilon_{My\lambda} C_{My} + \varepsilon_{H2O\lambda} C_{H2O}) L_{\mathit{eff}_{muscle},\lambda} + (\varepsilon_{melanin\lambda} C_{melanin} + \varepsilon_{HbO2\lambda} C_{HbO2} + \varepsilon_{Hb\lambda} C_{Hb} + \varepsilon_{H2O\lambda} C_{H2O}) L_{\mathit{eff}_{skin},\lambda} + (\varepsilon_{fat\lambda} C_{fat} + \varepsilon_{HbO2\lambda} C_{HbO2} + \varepsilon_{Hb\lambda} C_{Hb} + \varepsilon_{H2O\lambda} C_{H2O}) L_{\mathit{eff}_{fat},\lambda} + A_{muscle\ scat,\lambda} + A_{skin\ scat,\lambda} + A_{fat\ scat,\lambda} \qquad (4)$$

In order to compensate for the unknown variables in equation (4) above, the spectrometer 10 is configured to measure light attenuation at several different wavelengths. These unknown variables include all the chromophore concentrations, the effective light path lengths, and scattering attenuations. The absorptivity coefficients are known, and can be preprogrammed within the spectrometer. A simultaneous algebraic solution of equation (4) in which the number of wavelength specific attenuation measurements equals or exceeds the number of unknowns is possible, but has limitations. One limitation is that the absorbance of each chromophore may all increase or decrease together resulting in a co-linearity that causes the equation solution to become unstable as the number of wavelengths increases. Also, it is possible that different combinations of the unknown variables produce a similar solution resulting in an erroneous tissue oxygenation measurement. Another limitation of solving equation (4) for all the unknowns is related to the complexity and cost of the optical hardware needed to produce and measure the numerous wavelengths of light.

The number of unknown variables in equation (4) can be minimized so that the number of light sources, and hence attenuation measurements, can be minimized. If, for example, the tissue measurement site has skin, fat, and muscle layers, two photodetectors at different separation distances from the light sources can be used. If the attenuation measurements at the short (i.e., shallow) spacing provide a measurement depth contained within the skin and fat layers and the longer (i.e., deep) separation distance photodiode measures attenuation from skin, fat, and muscle, then subtracting the short distance attenuation from the simultaneously measured longer distance attenuation provides suppression or canceling of the skin and fat contributions. In this case, the skin and fat variables of equation (4) can be ignored and removed from the solution.

Another simplification of equation (4) can be made when the measurement tissue is mostly muscle and contains a limited number of chromophores that contribute to the overall attenuation. For example, the thenar eminence of the hand's palm, which is the muscle between lower thumb joint and the wrist, does not grow fat tissue like other areas of the body. Also, skin pigment or melanin is less variable on the palm surface. Furthermore, for muscle tissue, myoglobin and hemoglobin have a nearly indistinguishable profile of absorptivity versus wavelength, and both chromophores transport oxygen to tissue. Therefore, a common assumption for NIRS muscle measurements is that the tissue oxygenation represents combined hemoglobin and myoglobin effects with a majority of the signal being derived from hemoglobin. For this simplification, the $HbO_2$ and HHb abbreviations represent both hemoglobin and myoglobin. Wider separation distances between a light source and photodetector weight the optical path length and absorption to the deeper tissue depths that generally contain much more hemoglobin concentration than skin. Thus for large light source and photodetector separation distances, such as 15 mm or more, the skin variables of equation (4) may be ignored and removed from the solution.

Wavelength dependent scatter attenuation and chromophores other than hemoglobin/myoglobin and water generally have a constant slope or flatness within the NIRS wavelength region. For wavelengths that span a region in which the hemoglobin absorptivity coefficient is highly nonlinear with respect to wavelength, such as 680 to 800 nm, then the scattering attenuation and other chromophore attenuation contributions can be represented by a wavelength dependent slope and offset. For this simplification, the tissue's scattering attenuation and linear background absorbers can be represented as an unknown slope (m) and unknown offset (b) for a linear equation that relates wavelength (λ) to a tissue's background attenuation and absorption ($A_\lambda$) based on the following expression:

$$A_\lambda = m\lambda + b \quad (5)$$

Equations (3) to (5) can be arranged and combined to form a simplified equation in which the optical path lengths are predominately from muscle measurements, such as when using a 15 mm light source and photodetector separation located over the thenar eminence muscle:

$$A_\lambda = \ln\left(\frac{I_{in,\lambda}}{I_{in,\lambda}\exp^{\left(\frac{(\varepsilon_{HbO2\lambda}C_{HbO2}+\varepsilon_{Hb\lambda}C_{Hb}+\varepsilon_{H2O\lambda}C_{H2O})}{Leff_{tissue,\lambda}+m\lambda+b}\right)}}\right) \quad (6)$$

In equation (6) above, the right side of the equation is defined in terms of the incoming light intensity, allowing a wavelength compensation and correction integration calculation to be made that relies on pre-characterizing and predicting the wavelength and intensity characteristics of each light source, as set forth in equation (7) below:

$$A_{LED} = \ln\left(\frac{\sum_{\lambda min}^{\lambda max} I_{in,\lambda}}{\sum_{\lambda min}^{\lambda max} I_{in,\lambda}\exp^{((\mu_{a,\lambda})Leff_{tissue,\lambda}+m\lambda+b)}}\right) \quad (7)$$

where:

$\mu_{a,\lambda} = \varepsilon_{HbO2\lambda}C_{HbO2} + \varepsilon_{Hb\lambda}C_{Hb} + \varepsilon_{H2O\lambda}C_{H2O}$ is the tissues' wavelength dependent absorption coefficient represented as the summed product of each chromophore's absorptivity coefficient and concentration.

Equation (7) above relates attenuation measured with one light source and photodetector to the individual concentrations of significant, non-linear absorbing chromophores such as hemoglobin and water, and a composite of linear attenuators such as melanin or bilirubin. Including the numeric integration terms over the distribution of wavelengths ($\lambda_{min}$ to $\lambda_{max}$) contained within a light source appropriately weights the wavelength dependent variables to the exact wavelengths emitted into the tissue, thus enabling improved accuracy of the desired concentration measurements. Since thenar eminence tissue is robust to edema, the water concentration can be assumed constant, 70 wt %. Also, since effective path length for each wavelength can be predicted from additional modeling and pre-characterization, the unknowns of equation (7) reduces to four. As such, four light sources 46 each with different mean or central wavelengths are used by the spectrometer 10 to solve equation (7) and measure tissue hemoglobin concentrations and oxygenation levels.

Figure 4:
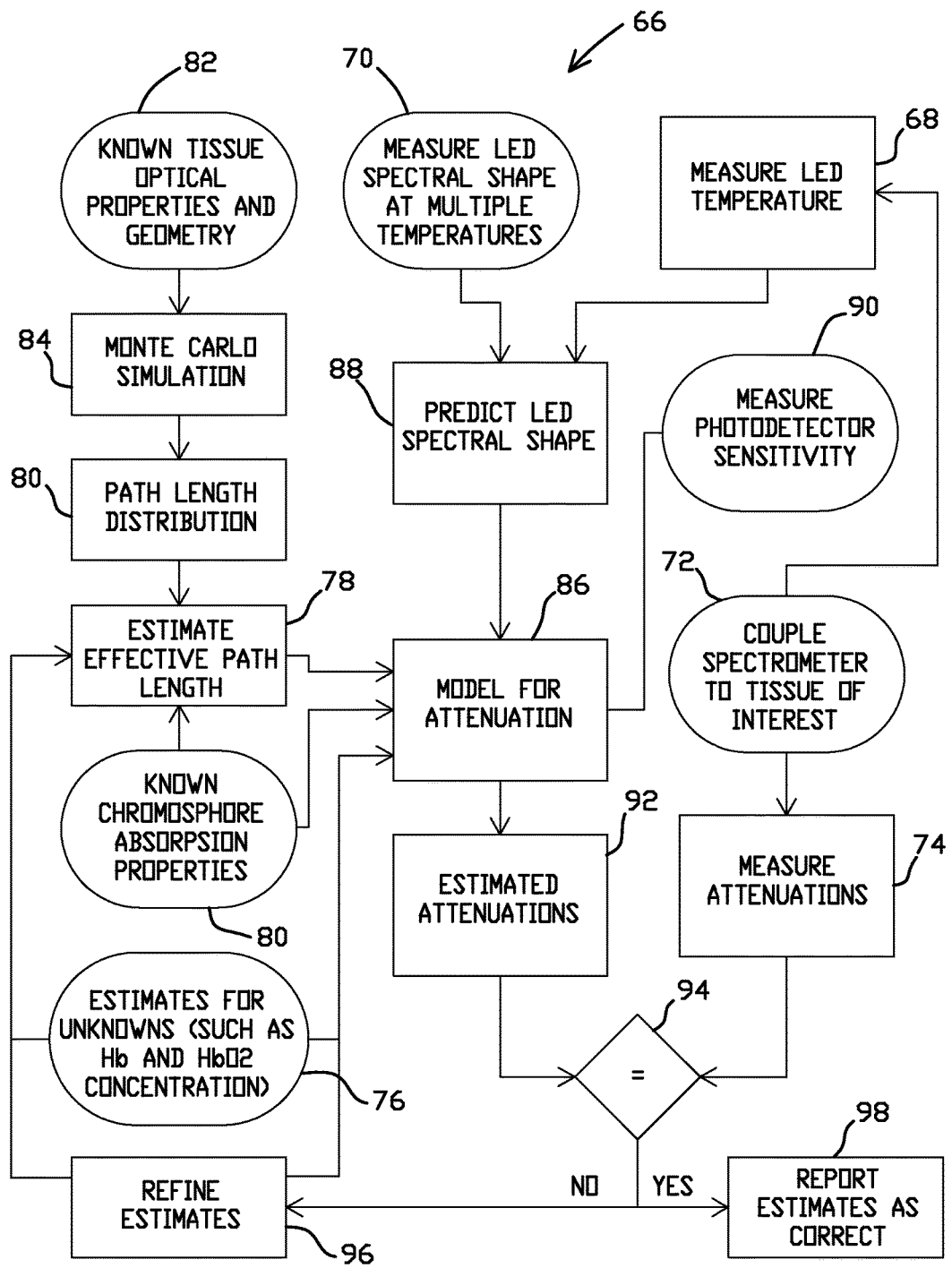
FIG. 4 is a flow diagram of a method for determining one or more tissue oxygen measurements in accordance with an illustrative embodiment.

FIG. 4 is a flow diagram of an illustrative method 66 for determining one or more tissue oxygen measurements in body tissue such as saturation oxygen level ($StO_2$) and/or chromophore concentration. The method 66 may represent, for example, an algorithm or routine run by the spectrometer 10 of FIGS. 1-2 to provide wavelength compensation and path length corrections needed to measure tissue oxygenation when the optical hardware of the spectrometer 10 does not control or precisely define the wavelengths of light emitted by the LEDs 46. In one embodiment, for example, the method 66 can comprise an algorithm or routine run by the processor 44 to compensate for wavelength and path length effects that result from the elimination of the light source conditioning optics used by some NIRS spectrometer devices.

The method 66 may begin generally at block 68, in which the operating temperature or voltage of a multiple wavelength light source is measured. With respect to the spectrometer of FIGS. 1-2, and in some embodiments, the operating temperature can be determined using the temperature sensor 54 coupled to the light source board 36. In other embodiments, the operating voltage can be sensed in lieu of temperature, which can then be used to derive the operating temperature of the LEDs 46.

The wavelength dependent intensity variable of equation (7) can be pre-characterized and calibrated using a calibration source (block 70). The calibration process can include, for example, obtaining a photodiode spectral shape reading from one or more of the LEDs 46 at one or more temperatures that can be used to correct for any temperature effect on the output response of equation (7). An example apparatus and process that can be used for pre-characterizing and calibrating the spectrometer's 10 light source and photodetector are described further herein with respect to FIGS. 6 and 7, respectively.

The spectrometer 10 can be coupled to a tissue of interest containing chromophore samples to be measured (block 72), which can be sensed via the first photodetector 40 and using the temperature and wavelength dependent light intensity or power values obtained from the calibration apparatus. At block 74, the tissue optical attenuation can then be empirically measured by at least one LED 46 and one photodetector 40 of the spectrometer 10.

In some embodiments, the spectrometer algorithm is configured to estimate or guess the amounts of tissue chromophores contained in the tissue of interest (block 76). In certain embodiments, for example, the algorithm may utilize equation (7) discussed herein to relate attenuation measured with the at least one LED and photodetector to the individual concentrations of significant, non-linear absorbing chromophores such as hemoglobin and water, and a composite of linear attenuators such as melanin, bilirubin, and scattering attenuation. Other means for estimating or guessing the amounts of tissue chromophores present in the tissue can also be employed.

In some embodiments, the spectrometer 10 may estimate the effective optical path length ($L_{eff,\lambda}$) of the traversed light within the tissue (block 78). To estimate $L_{eff,\lambda}$ for the wavelength distribution (i.e., spectral shape) of each photodiode light source, the algorithm may receive, as inputs, the estimated chromophore concentrations (block 76) and the known chromophore absorptive properties (block 80). The algorithm may also receive, as an input, the path length distribution (block 80) obtained by applying the known tissue light scattering properties and geometry of the tissue to be measured (block 82) to a Monte Carlo simulation model or the like (block 84). From these parameters, the spectrometer algorithm estimates the effective optical path length ($L_{eff,\lambda}$), and provides this estimate to a tissue light attenuation model (block 86). Since the wavelength characteristics of the LED are not precisely defined due to the elimination of light source conditioning optics, at block 88 the spectrometer algorithm also inputs estimates of the wavelength dependent power properties of the LED from the measured LED operating temperature sensed by the temperature sensor at block 68, and provides this as an input to the tissue light attenuation model. In some embodiments, the photodetector sensitivity can also be measured (block 90) and provided as an input to the tissue light attenuation model.

Based on the estimate of the effective optical path length ($L_{eff,\lambda}$) and the predicted light source power properties, the tissue light attenuation model predicts the light attenuation within the tissue (block 92). In certain embodiments, for example, the spectrometer 10 may predict the tissue light attenuation by solving for the light attenuation ($A_{LED}$) using the summation of discrete attenuation calculations (the numerical integration calculation expressed in equation (7)) over a distribution of wavelengths ($\lambda_{min}$ to $\lambda_{max}$) defined by the spectral shape of the LED. Thus, a unique light source intensity, path length, and absorptivity coefficient are input into the attenuation model for each wavelength increment defined by each light source's wavelength distribution or spectral shape. In some embodiments, the wavelength increments are smaller than the spectral width of each light source and the responsivity of the photodetector. An example of a non-linear optimization algorithm or routine that can be used for solving equation (7) is described further herein with respect to FIG. 7.

At decision block 94, the predicted tissue light attenuation is then compared against the measured tissue light attenuation to assess if the attenuation value matches or is within a useful degree of accuracy (e.g., ≤2% absolute difference). In some embodiments, for example, a match may be determined by performing a root mean square function on the data and determining whether a root mean square error is minimized, indicating the likelihood of a match. If no match is found, then new estimates for the chromophore amounts are selected by the spectrometer 10 (block 96) and the process of estimating an effective path length based on the known chromophore absorption and tissue light scattering properties and the predicted light source power properties is applied to the tissue light attenuation model to generate another predicted value of the tissue light attenuation. In some embodiments, this process is an iterative solving process that is repeated multiple times until the predicted attenuation values match or are sufficiently close to the measured tissue light attenuation values.

If, on the other hand, the spectrometer 10 determines that the predicted tissue light attenuation matches or is within a useful degree of accuracy, the spectrometer 10 may display and trend the correctly predicted chromophore concentrations (block 98). For example, and in some embodiments, the spectrometer 10 may display the tissue chromophore amounts on a display screen coupled to the spectrometer 10. The tissue chromophore amounts can also be converted into other forms such as $StO_2$, allowing the physician to quickly determine, in real-time, the $StO_2$ level within the tissue. To determine and display an $StO_2$ value, for example, the spectrometer 10 would perform the method 66 for two chromophores relating to oxy and deoxy hemoglobin. Historical data taken over a period of time may also be displayed on the display screen, providing the physician with trending data related to changes in the patient's health status over time.

Figure 5:
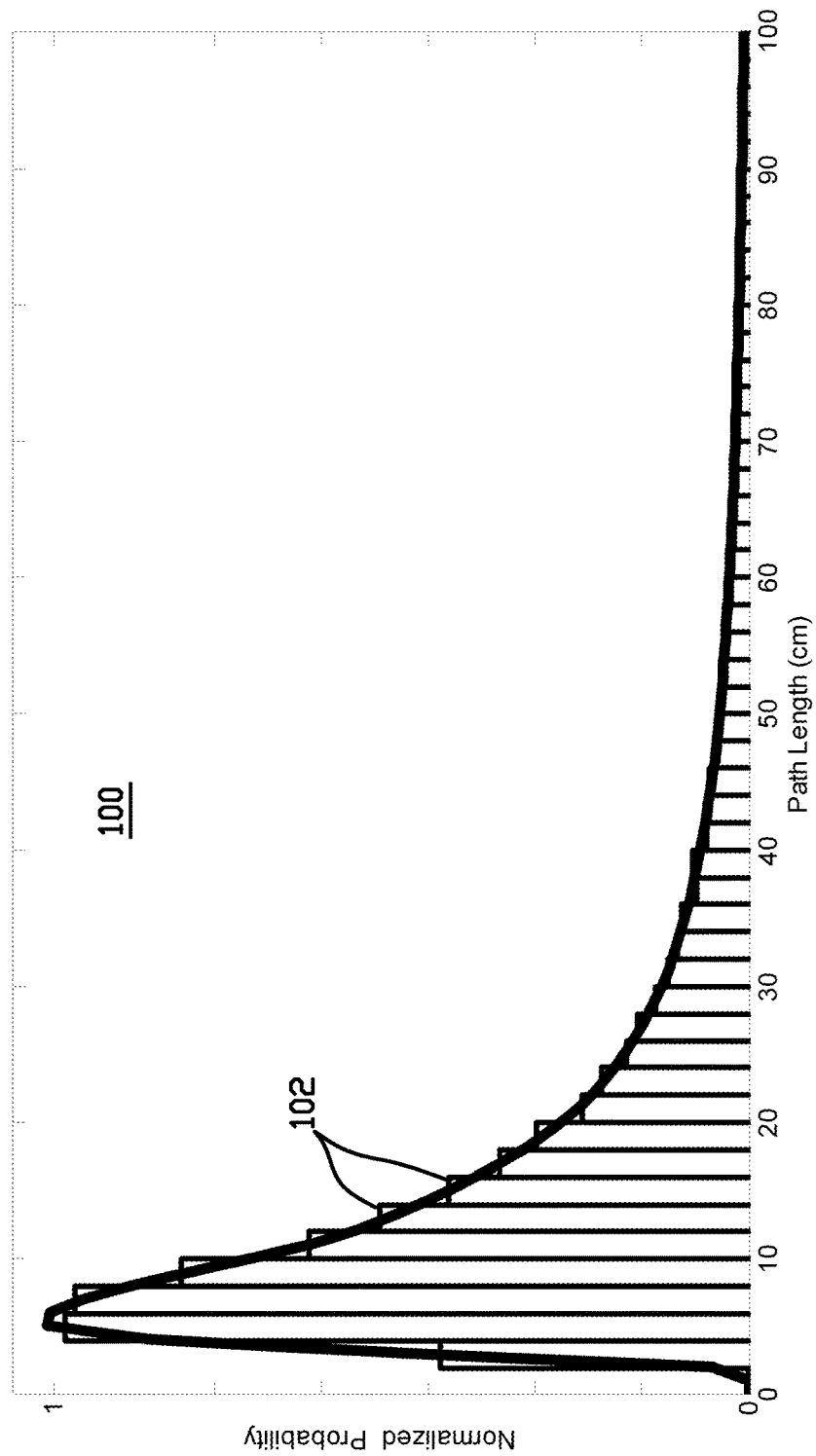
FIG. 5 is a graph showing an example of a modeled path length distribution for a given light source and detector spacing and a given tissue layer.

FIG. 5 is an example graph 100 showing path length distribution of sample light rays 102 through body tissue obtained by Monte Carlo simulation modeling. FIG. 5 may represent, for example, a normalized graph 100 of path length distribution of light rays 102 in body tissue in which the absorption coefficient ($\mu_a$) is near zero, the scattering coefficient ($\mu_s'$) is 8 cm$^{-1}$, the effective optical path length ($L_{eff,\lambda}$) is 19 cm$^{-1}$, and the light source to photodetector spacing is 15 mm.

To simulate light traveling in tissue, the Monte Carlo simulation model can be used by the spectrometer to determine and record the position of a light ray after each scattering event. The Monte Carlo model can be used, for example, for predicting light energy penetration within a tissue such as in radiation or photodynamic therapy where the optimal light energy or dose is dependent upon knowing a tissue's optical properties. Also, if tissue light attenuation is known, then the Monte Carlo model can be used to measure tissue optical properties, such as absorption or scattering, to help identify tissue pathologies such as cancer. In some embodiments, the Monte Carlo model can be used to obtain a distribution of light intensities or flux striking the photodetector for an anticipated range of scattering conditions with a fixed absorption coefficient that is at or near zero, and based on a fixed spacing between the light source and photodetector. In some embodiments, the simulation can be performed by a software program, firmware, and/or hardware. In one embodiment, for example, the simulation can be performed by a software program such as TRACEPRO® available from Lambda Research Corporation of Littleton, Mass.

The Monte Carlo model requires a number of input variables, including light source variables such as location, wavelength, illumination area, and angular distribution; detector variables such as viewing angle, detector area, and location; and tissue boundary and optical properties such as width, depth, shape, refractive index, absorption, scattering, and anisotropy. Based on these input variables, the Monte Carlo model launches light photons into the simulated tissue and then determines and tracks the stepwise movement of the photons that reach the photodetector. The photon's step size is randomly sampled from a probability distribution for the free path between tissue interaction events and launched into the tissue. The inverse value of the mean free path equals the transport scattering coefficient. At the end of a photon step movement, the photon number or intensity is attenuated according to the absorption properties per unit path length (i.e., the absorption coefficient).

After absorption, a new photon direction is randomly chosen from a probability distribution for the deflection angle of the scattered light using the tissue's anisotropy coefficient. This process can be repeated one or more times until either the photon reaches the photodetector or is eventually lost such as being fully absorbed or exiting the tissue boundary. The software program then returns the intensity of each light ray that exits the tissue where the photodetector is located.

The light intensity distribution for the numerous photon or ray simulations is then used in combination with the Beer-Lambert Law to calculate the effective optical path length. From the Beer-Lambert Law, and in some embodiments, the effective optical path length of each detected ray ($L_{RAY}$) can be calculated based on the following equation:

$$L_{RAY} = \log(I_0/I_{RAY})/\mu_a \quad (8)$$

where $I_0=1$ and ($\mu_a$) is the absorption coefficient.

A constant absorption coefficient ($\mu_a$) such as 0.01 can be used in equation (8) above so that the Monte Carlo simulation is performed only for the differing scattering properties of tissue, thereby significantly decreasing the number of required simulations. This can be accomplished because equation (8) can be used to define the effective path lengths at the differing absorption coefficient values.

From the Beer-Lambert Law, the intensity of each detected light ray ($L_{RAY}$) may be calculated for numerous absorption coefficient values ($\mu_a$) that are not zero, and which span the range of probable tissue values. By way of example and not limitation, $L_{RAY}$ may be solved for 43 μa values ranging from 0.001 to 11.7 using the following equation:

$$I_{RAY} = I_0 \exp(-(\mu_a(L_{RAY}))) \qquad (9)$$

The effective optical path length ($L_{eff,\lambda}$) can then be calculated for each of the $\mu_a$ conditions from equation (9) above as follows:

$$L_{eff,\lambda} = \frac{\text{Ln}\left(\sum I_0 / \sum I_{Ray}\right)}{\mu_{a,\lambda}} \qquad (10)$$

The process can be repeated for the simulated media having scattering properties resembling tissue at different wavelengths. The absorption and transport scattering coefficients $\mu_a$ and $\mu_s'$ have units of reciprocal path length (cm$^{-1}$), and for tissue typically range from 0 cm$^{-1}$ to 0.5 cm$^{-1}$ and 5 to 10 cm$^{-1}$, respectively. As an example, the process may be repeated for different wavelengths at $\mu_s'$ of 5, 8, and 10 cm$^{-1}$.

The effective optical path length ($L_{eff,\lambda}$) can be obtained for a variety of optical absorption ($\mu_a$) and scattering coefficient ($\mu_s'$) properties. Since $\mu_a$ equals the product of the chromophore concentration (C) and chromophore absorption coefficient (ε), the estimated chromophore concentration and known absorption coefficient that are inputted into the tissue attenuation model can be used to select an appropriate $L_{eff,\lambda}$ for a given wavelength of light. The wavelength of the light also defines the appropriate μs' when selecting $L_{eff,\lambda}$.

In some embodiments, the Monte Carlo model is configured to generate a two dimensional lookup table that outputs the effective optical path length for the following input values of absorption coefficient ($\mu_{a,\lambda}$) and transport scattering coefficient ($\mu'_{s,\lambda}$) for a given wavelength ($\lambda$):

$$\mu_{a,\lambda} = \sum_i (\varepsilon_{i,\lambda} C_i); \qquad (11)$$

where i=each measured chromophore concentration; and $$\mu'_{s,\lambda} = \mu_{s,\lambda}(1-g); \qquad (12)$$

where $\mu_{s,\lambda}$ is the scattering coefficient and g is the anisotropy coefficient of the tissue. Tissue anisotropy coefficient (g) values are typically near 0.90, indicating that tissue scattering occurs mostly in the forward direction.

Other techniques for modeling the relationship of the effective optical path length versus the absorption and scatter coefficients can also be employed. In one alternative embodiment, for example, a Monte Carlo technique can be performed on thousands of rays for several scattering conditions in order to directly obtain a distribution of optical path lengths (e.g., $L_{RAY}$ of equation (8)) without having to model and define the intensity distribution of each ray. In another embodiment, a time-resolved system can be used to empirically measure light path length distribution using tissues or tissue phantoms having controlled and known scattering profiles.

Figure 6:
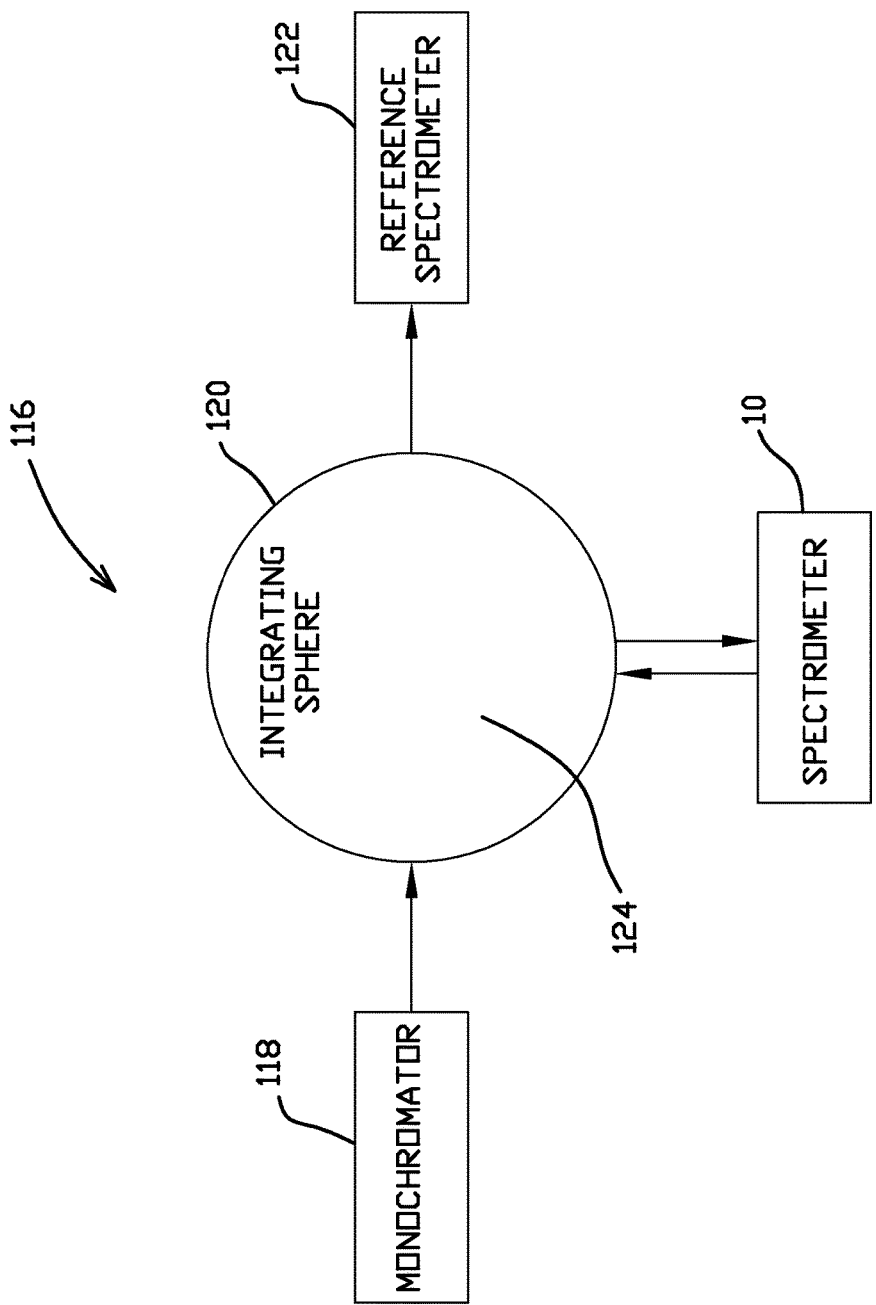
FIG. 6 is a schematic view of a calibration apparatus in accordance with an illustrative embodiment.

FIG. 6 is a schematic view of an example calibration apparatus 116 for calibrating the spectrometer 10 of FIG. 2 in order to predict the wavelength dependent power output of an LED source 46 as a function of temperature and/or operating voltage. In some embodiments, for example, the calibration apparatus 116 can also be used for calibrating the spectrometer photodetector as part of the calibration step (block 70) described with respect to FIG. 4.

As shown in FIG. 6, the calibration apparatus 116 includes a monochromator 118, an integrating sphere 120 coupled to a spectrometer 10 including at least one light source and photodetector to be characterized, and a reference spectrometer 122 that is substantially linear over a wide dynamic range. If the photodetector calibration is not required, such as when the photodetector's spectral response is not significantly different over the wavelength region of interest, then the monochromator 118 would not be needed.

The monochromator 118 serves as a wavelength calibration source, and is configured to transmit a sufficiently narrow wavelength band of light into the integrating sphere 120. In some embodiments, for example, the monochromator 118 is configured to transmit light having a bandwidth at or less than about 1 nm. The integrating sphere 120 includes a hollow cavity 124 that is coated for high diffuse reflectivity, and serves as a diffuser to provide uniform scattering of the light rays received by the tissue oxygenation and reference spectrometers 10, 122.

Figure 7:
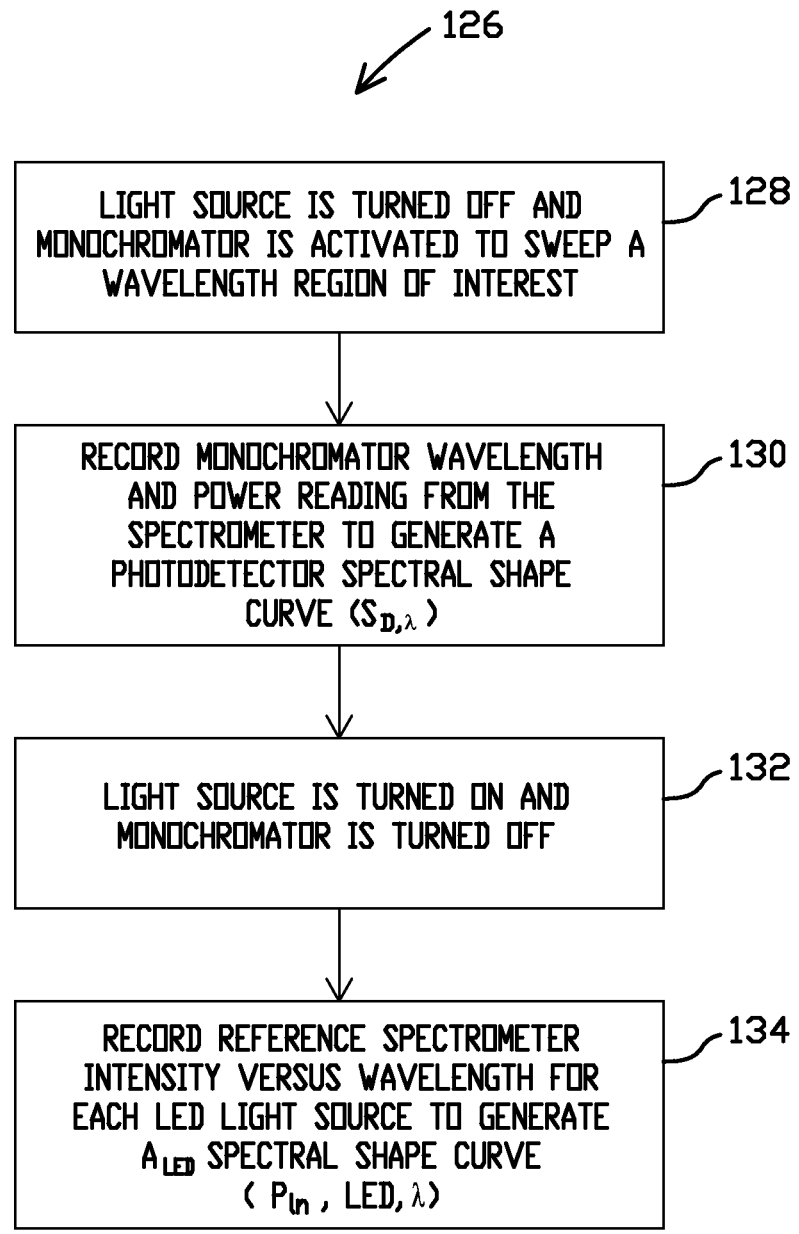
FIG. 7 is a flow diagram of an example process for measuring the power of a light source as a function of temperature and/or operating voltage using the apparatus of FIG. 6.

FIG. 7 is a flow diagram of an example process 126 for predicting the wavelength specific power of an LED light source as a function of temperature and/or operating voltage using the calibration apparatus 116 of FIG. 6. FIG. 7 may represent, for example, several illustrative steps that can be used for determining the light source wavelength dependent power properties of each LED 46 used by the spectrometer 10 of FIG. 2.

The process 126 can begin generally at block 128, in which the LED to be characterized is turned off, and the monochromator 118 is activated to sweep a wavelength region of interest. At each step during the sweep, the apparatus 116 records the monochromator wavelength and power reading from the reference spectrometer 122 (e.g., as watts), and the relative intensity of the tissue oxygenation photodetector as digital counts. The output of this step provides a photodetector spectral shape curve ($S_{D,\lambda}$) in counts per watt for each photodetector, as shown, for example, in the bottom curve of FIG. 8. In another step, the monochromator 118 is turned off and the LED 46 to be characterized for the tissue oxygenation spectrometer 10 is turned on (block 132). The reference spectrometer 122 records the intensity versus wavelength data for the LED at a certain temperature (block 134). The intensity and wavelength values of this step may provide an LED spectral shape curve ($P_{LED,\lambda}$) such as that shown, for example, in FIGS. 8 and 9.

Figure 8:
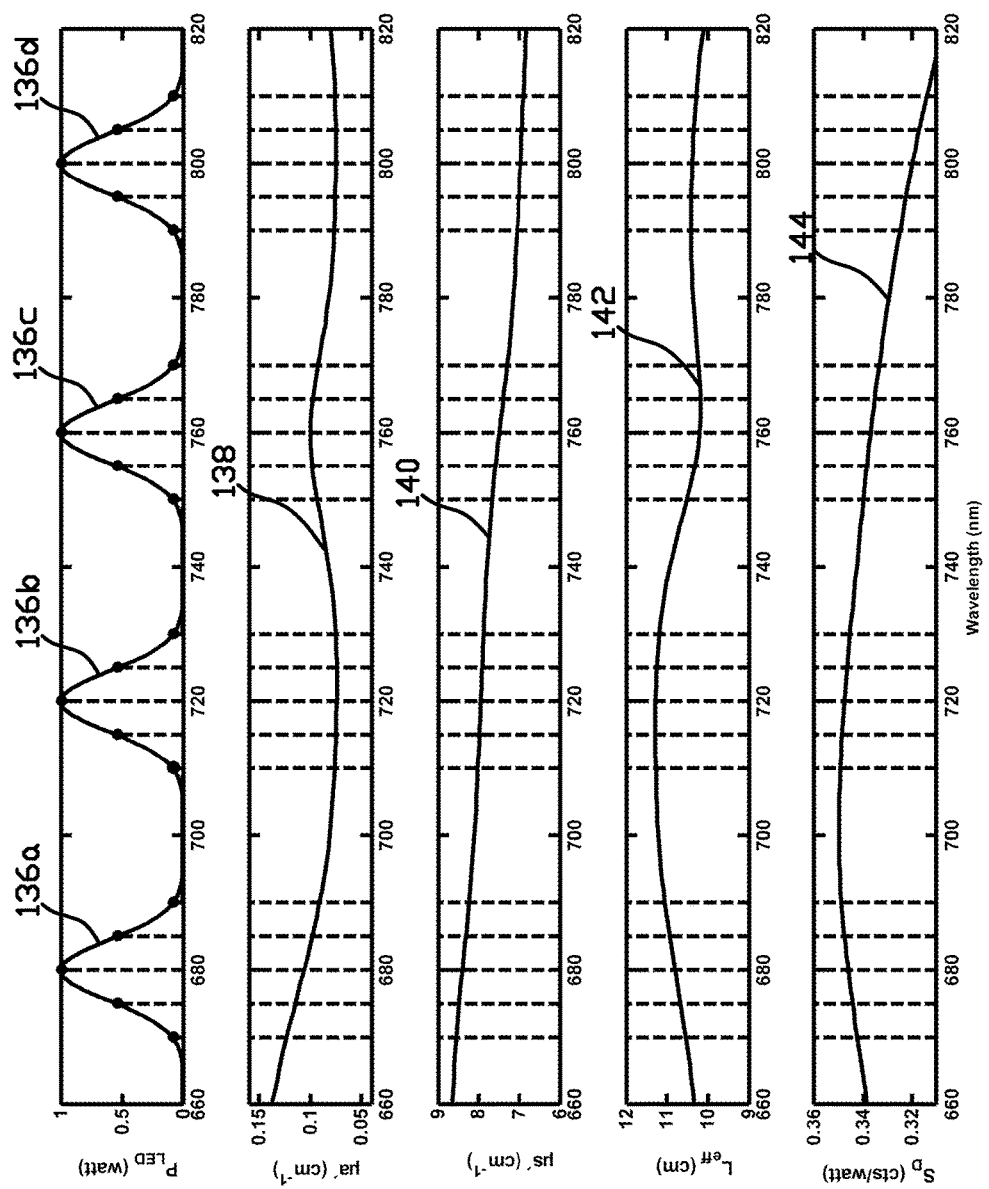
FIG. 8 depicts a number of graphs including several example spectral shape curves for multiple LED light sources, the absorption coefficient of muscle tissue at 70% water and 50% tissue oxygen saturation, the scattering coefficient of muscle tissue, the effective path length, and photodetector sensitivity.

FIG. 8 depicts a number of graphs including several example spectral shape curves 136a-136 for multiple LED light sources ($P_{LED}$), the absorption coefficient of muscle tissue at 70% water and 50% tissue oxygen saturation 138 ("$\mu_a$'"), the scattering coefficient of muscle tissue 140 ("$\mu_s$'"), the effective path length 142 ("$L_{eff}$"), and photodetector sensitivity 144 ("$S_D$"). The output spectral shape curve from the characterization process 126 of FIG. 7 can be used in conjunction with the absorptivity and scattering properties corresponding to each wavelength increment (as indicated by the dashed vertical lines in FIG. 8) to predict the LED signal attenuation ($A_{LED}$) at a particular temperature that is numerically solved over the entire wavelength range of each LED employed by the spectrometer 10, as indicated in equation (13) below:

$$A_{LED} = \ln\left(\frac{\sum\limits_{\lambda min}^{\lambda max} P_{LED,\lambda}S_{D,\lambda}}{\sum\limits_{\lambda min}^{\lambda max} P_{LED,\lambda}S_{D,\lambda}\exp^{((\mu_{a,\lambda})Leff_{tissue,\lambda}+m\lambda+b)}}\right) \quad (13)$$

Any scaling LED power or photodetector sensitivity scalar variable that is not wavelength specific is factored out of the numerically solved integral in both the numerator and denominator portion of equation (13), and thus would cancel out.

The characterization process 126 can then be repeated for multiple different temperatures in order to determine the relative intensity and wavelength values of the LED ($P_{LED, \lambda}$) across a temperature spectrum. In some embodiments, for example, the calibration apparatus 116 is configured to record this information over a large number of temperatures (e.g., one value every 1° C.), and use the closest data based on the measured temperature.

In another embodiment, the information is recorded over only a few temperatures (e.g., the low and high temperature extremes), and the data is interpolated to obtain a result in between. To correctly compensate for the LED spectral shape, each point along the spectral distribution should be interpolated or extrapolated rather than just being shifted based on the peak or centroid of the response curve. This is due to the non-linear temperature characteristics of the LED. For example, as the LED is heated, the LED experiences not only a shift towards a longer wavelength, but the distribution is also broadened and the peak intensity of the light is reduced. Conversely, as the LED is cooled, the LED experiences a shift towards a shorter wavelength, a narrowing of the distribution, and a larger peak intensity.

To compensate for these LED spectral shape distortions at different temperatures, a normalization process can be performed on the spectral shapes for each of the "hot" and "cold" temperature values. In some embodiments, for example, the "hot" and "cold" spectral shapes can be first normalized based on their peak intensity, and the intensity and wavelength axes can be transposed prior to interpolation to predict the LED spectral shape at any given LED operating temperature.

Figure 9:
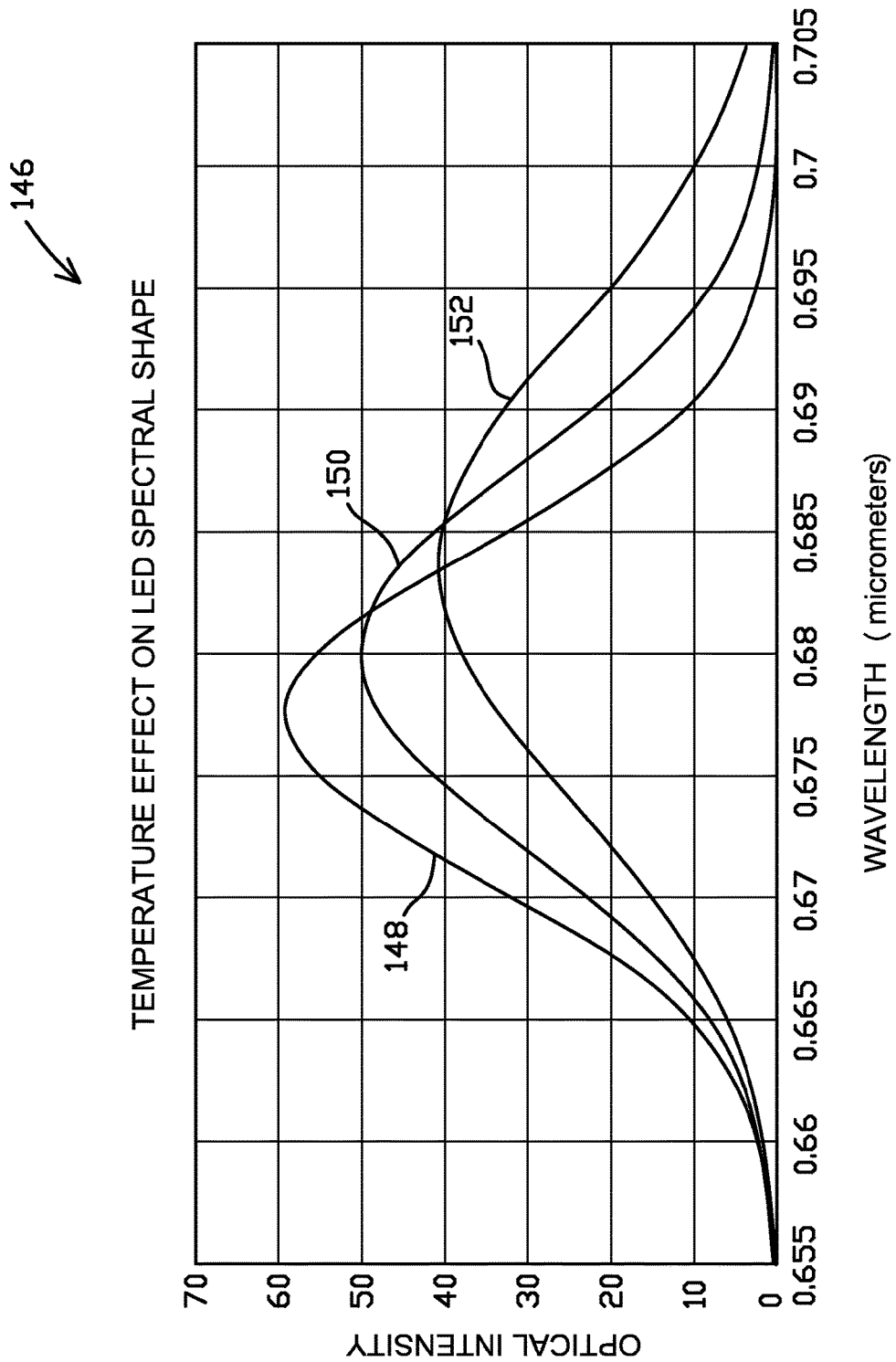
FIG. 9 is a graph showing the spectral shape curve of an LED at three different temperatures.
Figure 10:
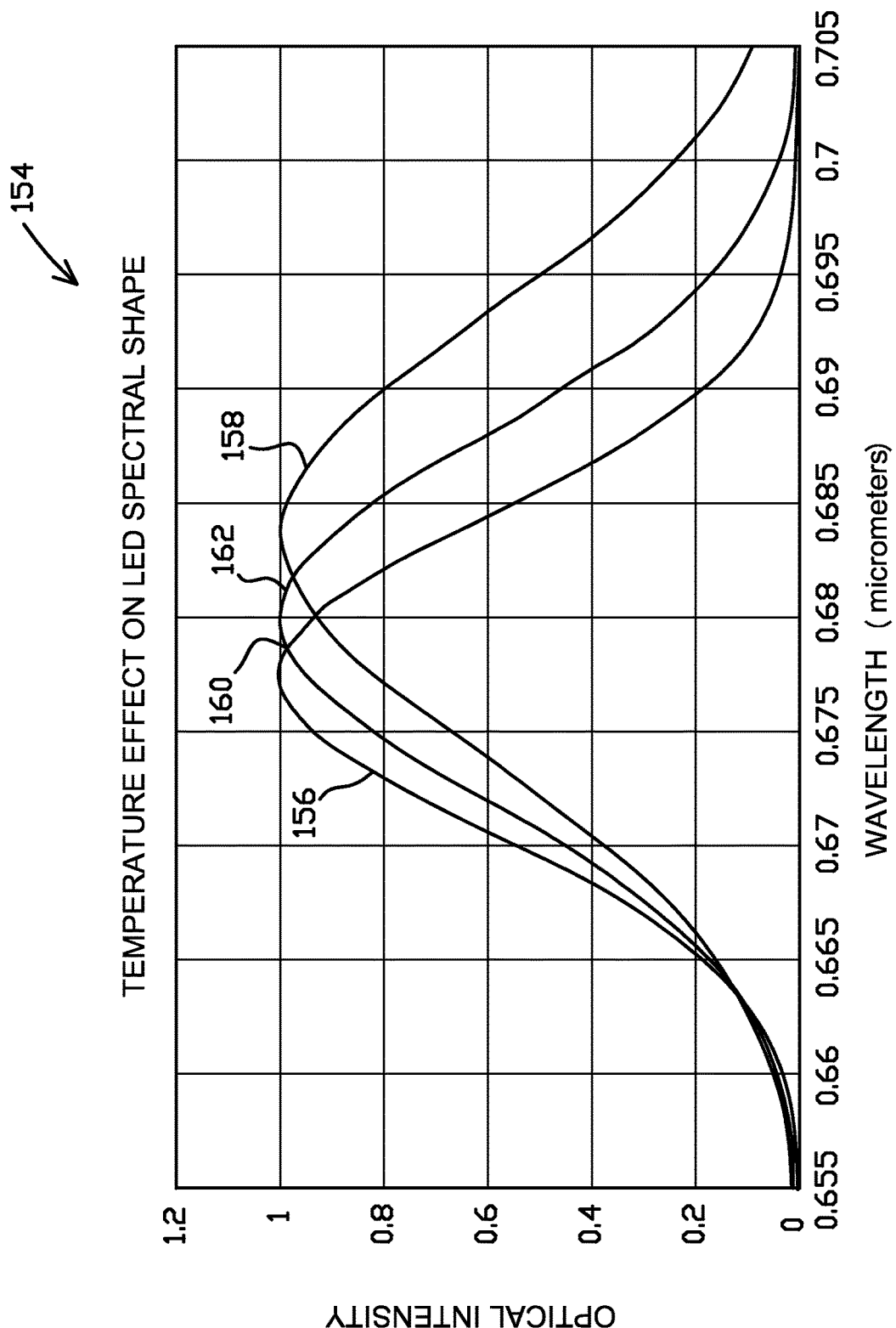
FIG. 10 is a graph comparing the spectral shape curves of an LED measured at 22° C. and predicted at 22° C. after a normalization and interpolation process has been performed on the spectral response curves measured at 10° C. and 40° C.

FIGS. 9-10 are several graphs showing the spectral shape of optical intensity versus wavelength for an LED at two different temperatures, representing the lower and upper bounds of the operating temperature of the LED. In a first graph 146 shown in FIG. 9 prior to any compensation, the spectral response curve 148 for the LED operating at a relatively cold temperature (e.g., at 10° C.) is shifted to the left of the room temperature response curve 150 of the LED (e.g., at 22° C.). A second spectral response curve 152 associated with the LED operating at a relatively hot temperature (e.g., 40° C.), in turn, is shifted to the right of the actual response curve 150. In addition, and as can be further seen in FIG. 9, the shape of the spectral response curve 148 for the relatively cold LED is narrower and has a larger peak optical intensity than that of the spectral response curve 152 for the relatively hot LED, which has a broader shape with a smaller peak optical intensity.

FIG. 10 is a graph 154 showing the spectral shape curves of the LEDs after a normalization and interpolation process has been performed on the peak intensity and wavelength values. As shown in FIG. 10, when normalized spectral response curves 156, 158 for the 10° C. and 40° C. LEDs are generated, an interpolation of the two curves 156, 158 along a line of uniform intensity generates a predicted spectral response curve 160 at 22° C. that closely matches the actual measured spectral shape curve 162 of the LED at 22° C.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A near infrared spectrometer for sensing tissue oxygen measurements in body tissue, comprising:
   a plurality of light sources configured to emit broadband, near infrared measurement light into body tissue;
   a mixer positioned such that the plurality of light sources emit the measurement light directly into the mixer without passing through any light conditioning filter located between the mixer and the plurality of light sources;
   at least one temperature sensor configured to sense at least one temperature of the plurality of light sources;
   at least one broadband photodetector configured for sensing at least a portion of the measurement light reflected back from the body tissue; and
   a processor configured to:
   model light attenuations within the body tissue based at least in part on the at least one temperature;
   predict at least one light attenuation value within the body tissue based on the modeled light attenuation; and
   estimate at least one tissue chromophore concentration within the body tissue by comparing attenuations of the sensed measurement light reflected back from the body tissue to the at least one predicted light attenuation value,
   wherein the at least one predicted light attenuation value comprises a plurality of predicted light attenuation values at a plurality of wavelength increments, wherein the processor is configured to sum the plurality of predicted light attenuation values, wherein the wavelength increments are smaller than a spectral width of each light source and a responsivity of the at least one broadband photodetector.

2. The spectrometer of claim 1 wherein the modeling of the light attenuations compensates for a spectral shape of each light source based at least in part on the at least one temperature.

3. The spectrometer of claim 2, wherein the spectral shape of each light source is pre-characterized at a plurality of temperatures.

4. The spectrometer of claim 3, wherein the spectral shape of each light source is interpolated or extrapolated from a plurality of pre-characterized temperatures.

5. The spectrometer of claim 1, wherein a path length distribution for each wavelength increment of the measurement light is predicted using a simulation model.

6. The spectrometer of claim 5, wherein the simulation model is a Monte Carlo model.

7. A near infrared spectrometer for sensing tissue oxygen measurements in body tissue, comprising:
   a plurality of light sources configured to emit broadband, near infrared measurement light into body tissue;
   a mixer positioned such that the plurality of light sources emit the measurement light into the mixer without passing through any light conditioning filter located between the mixer and the plurality of light sources;

at least one broadband photodetector configured for sensing at least a portion of the measurement light reflected back from the body tissue;

at least one temperature sensor configured for sensing at least one temperature of the light sources; and a processor configured to:
  model light attenuations within the body tissue based at least in part on the at least one temperature;
  estimate at least one tissue chromophore concentration within the body tissue by comparing attenuations of the sensed measurement light reflected back from the body tissue to the modeled light attenuations; and
  sum the modeled light attenuations in tissue at a plurality of wavelength increments, the wavelength increments being smaller than a spectral width of each light source and a responsivity of the at least one broadband photodetector.

8. A method for determining one or more tissue oxygen measurements in body tissue, the method comprising:
  coupling a spectrometer to a tissue of interest, the spectrometer including:
  a plurality of light sources configured to emit broadband, near infrared measurement light into the body tissue;
  at least one temperature sensor configured to sense at least one temperature of the light sources;
  a mixer positioned such that the plurality of light sources emit the measurement light into the mixer without passing through any light conditioning filter located between the mixer and the plurality of light sources;
  a processor; and
  at least one broadband photodetector configured for sensing at least a portion of the measurement light reflected back from the body tissue;

measuring the attenuation of the measurement light reflected back from the body tissue using the at least one broadband photodetector;

predicting light attenuation within the body tissue using the processor, the predicted light attenuation predicted based on the at least one temperature and a light attenuation model;

summing a plurality of predicted attenuations of light in tissue at a plurality of wavelength increments, the wavelength increments being smaller than a spectral width of each light source and a responsivity of the at least one broadband photodetector; and estimating, using the processor, at least one tissue chromophore concentration within the body tissue by comparing the attenuation of the measurement light reflected back from the body tissue to the predicted light attenuation, wherein the modeling of the light attenuation compensates for a spectral shape of each light source based at least in part on the at least one temperature.

* * * * *